US005436142A

United States Patent [19]
Wigler et al.

[11] Patent Number: 5,436,142
[45] Date of Patent: Jul. 25, 1995

[54] METHODS FOR PRODUCING PROBES CAPABLE OF DISTINGUSHING VARIANT GENOMIC SEQUENCES

[75] Inventors: Michael Wigler, Lloyd Harbor; Nikolai Lisitsyn, Spring Harbor, both of N.Y.

[73] Assignee: Cold Spring Harbor Laboratory, Colds Spring Harbor, N.Y.

[21] Appl. No.: 974,447

[22] Filed: Nov. 12, 1992

[51] Int. Cl.$^6$ ............................................. C12P 19/34
[52] U.S. Cl. ...................... 435/91.2; 435/6; 536/24.3; 536/24.31; 935/78
[58] Field of Search ................ 435/91.2, 6; 536/24.31, 536/24.3; 935/78

[56] References Cited

PUBLICATIONS

Welcher et al., *Nucleic Acids Res.* 14(24), 10027–10044 (1986).
Bjourson et al., *Appl. Environ. Micro.* 54(11), 2852–2855 (1988).
Lisitsyn et al., *Science* 259, 946–951 (1993).
Lamar and Palmer (1984) Y-encoded, species-specific DNA in mice: evidence that the Y chromosome exists in two polymorphic forms in inbred strains. Cell 37:171–177.
Kunkel, et al. (1985) Specific cloning of DNA fragments absent from the DNA of a male patient with an X chromosome deletion. Proc. Natl. Acad. Sci. USA 82:4778–4782.
Nussbaum, et al. (1987) Isolation of anonymous DNA sequences from within a submicroscopic X chromosomal deletion in a patient with choroideremia, deafness, and mental retardation. Proc. Natl. Acad. Sci. USA 84:6521–6525.
Wieland, et al. (1990) A method for difference cloning: gene amplification following subtractive hybridization. Proc. Natl. Acad. Sci. USA 87:2720–2724.
Straus and Ausubel (1990) Genomic subtraction for cloning DNA corresponding to deletion mutations. Proc. Natl. Acad. Sci. USA 87:1889–1893.
Wieland, et al. (1992) Isolation of DNA sequences deleted in lung cancer by genomic difference cloning. Proc. Natl. Acad. Sci. USA 89:9705–9709.

*Primary Examiner*—Margaret Parr
*Assistant Examiner*—Kenneth R. Horlick
*Attorney, Agent, or Firm*—Bertram I. Rowland

[57] ABSTRACT

Methodology is provided for developing probes for identifying sequence differences between two related DNA populations, sets of DNA fragments or collections of restriction-endonuclease-cleaved DNA. The method employs an initial stage to obtain a representation of both DNA populations, namely using the PCR to produce relatively short fragments, referred to as amplicons. Tester amplicons containing target DNA, sequences of interest, are ligated to adaptors and mixed with excess driver amplicons under melting and annealing conditions, followed by PCR amplification. The process may be repeated so as to greatly enrich the target DNA. Optionally, the target DNA may then be cloned and the DNA used as probes.

14 Claims, No Drawings

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

AGCACTCTCC AGCCTCTCAC CGCA 24

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GATCTGCGGT GA 12

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

ACCGACGTCG ACTATCCATG AACA 24

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GATCTGTTCA TG 12

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AGGCAACTGT GCTATCCGAG GGAA  24

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GATCTTCCCT CG  12

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

AGCACTCTCC AGCCTCTCAC CGAG  24

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GATCCTCGGT GA  12

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

ACCGACGTCG ACTATCCATG AACG  24

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GATCCGTTCA TG  12

(2) INFORMATION FOR SEQ ID NO:11:

(i) SEQUENCE CHARACTERISTICS:

( A ) LENGTH: 24 base pairs
                    ( B ) TYPE: nucleic acid
                    ( C ) STRANDEDNESS: single
                    ( D ) TOPOLOGY: linear ( i i ) MOLECULE TYPE: cDNA ( x i ) SEQUENCE DESCRIPTION: SEQ ID NO:11:

AGGCAACTGT GCTATCCGAG GGAG                                                      24

( 2 ) INFORMATION FOR SEQ ID NO:12:

( i ) SEQUENCE CHARACTERISTICS:
                    ( A ) LENGTH: 12 base pairs
                    ( B ) TYPE: nucleic acid
                    ( C ) STRANDEDNESS: single
                    ( D ) TOPOLOGY: linear ( i i ) MOLECULE TYPE: cDNA ( x i ) SEQUENCE DESCRIPTION: SEQ ID NO:12:

GATCCTCCCT CG                                                                   12

( 2 ) INFORMATION FOR SEQ ID NO:13:

( i ) SEQUENCE CHARACTERISTICS:
                    ( A ) LENGTH: 12 base pairs
                    ( B ) TYPE: nucleic acid
                    ( C ) STRANDEDNESS: single
                    ( D ) TOPOLOGY: linear ( i i ) MOLECULE TYPE: cDNA ( x i ) SEQUENCE DESCRIPTION: SEQ ID NO:13:

AGCTTGCGGT GA                                                                   12

( 2 ) INFORMATION FOR SEQ ID NO:14:

( i ) SEQUENCE CHARACTERISTICS:
                    ( A ) LENGTH: 12 base pairs
                    ( B ) TYPE: nucleic acid
                    ( C ) STRANDEDNESS: single
                    ( D ) TOPOLOGY: linear ( i i ) MOLECULE TYPE: cDNA ( x i ) SEQUENCE DESCRIPTION: SEQ ID NO:14:

AGCTTGTTCA TG                                                                   12

( 2 ) INFORMATION FOR SEQ ID NO:15:

( i ) SEQUENCE CHARACTERISTICS:
                    ( A ) LENGTH: 24 base pairs
                    ( B ) TYPE: nucleic acid
                    ( C ) STRANDEDNESS: single
                    ( D ) TOPOLOGY: linear ( i i ) MOLECULE TYPE: cDNA ( x i ) SEQUENCE DESCRIPTION: SEQ ID NO:15:

AGGCAGCTGT GGTATCGAGG GAGA                                                      24

( 2 ) INFORMATION FOR SEQ ID NO:16:

( i ) SEQUENCE CHARACTERISTICS:
                    ( A ) LENGTH: 12 base pairs
                    ( B ) TYPE: nucleic acid
                    ( C ) STRANDEDNESS: single
                    ( D ) TOPOLOGY: linear ( i i ) MOLECULE TYPE: cDNA ( x i ) SEQUENCE DESCRIPTION: SEQ ID NO:16:

AGCTTCTCCC TC    12

METHODS FOR PRODUCING PROBES CAPABLE OF DISTINGUSHING VARIANT GENOMIC SEQUENCES

This invention was made with Government support under contract OIG-5R CA39829-08 awarded by the National Institute of Health. The Government has certain rights in this invention.

TECHNICAL FIELD

The field of this invention is genomic analysis.

BACKGROUND

Comparative genomic DNA analysis holds promise for the discovery of sequences which may provide for information concerning polymorphisms, infectious DNA based agents, lesions associated with disease, such as cancer, inherited dominant and recessive traits, and the like. By being able to detect particular DNA sequences which have a function or affect a function of cells, one can monitor pedigrees, so that in breeding animals one can follow the inheritance of particular sequences associated with desirable traits. In humans, there is substantial interest in forensic medicine, diagnostics and genotyping, and determining relationships between various individuals. There is, therefore, substantial interest in providing techniques which allow for the detection of common sequences between sources and sequences which differ between sources.

The mammalian genome is extraordinarily large, having about $10^9$ bp. The human genome project has initiated an effort to map and sequence the entire genome. However, much of the early work will be directed more toward determining the site of particular genes, than determining contiguous sequences of a particular chromosome. It will be of substantial interest to know whether there will be substantial uniformity in segments of the population as to particular sequences, as compared to finding substantial differences in various population subsets.

Because of the complexity of the human genome, there is a very substantial handling and processing problem with the human genomic DNA. In order to deal with such a large amount of DNA, one must develop processes which allow for simplification and selection, while still providing the desired information. Therefore, efforts must be made which will provide for opportunities which will allow to greater or lesser degrees, dissecting portions of a genome of interest, where comparisons can be made between two different sources of DNA.

RELEVANT LITERATURE

Efforts at difference analysis at the level of the genome are described by Lamar and Palmer, *Cell* 37, 171 (1984); Kunkel, et al., *Proc. Natl. Acad. Sci. USA* 82, 4778 (1985); Nussbaum, et al., *Proc. Natl. Acad. Sci. USA* 84, 6521 (1987); Wieland, et al., *Proc. Natl. Acad. Sci. USA* 87, 2720 (1990); Straus and Ausubel, *Proc. Natl. Acad. Sci. USA* 87, 1889 (1990).

SUMMARY OF THE INVENTION

Representational difference analysis is provided to determine similarities or differences between two related sources of DNA. In a first step, a representative portion of each genome is prepared, using a restriction endo-nuclease (RE1), ligation of partially double-stranded adaptors, and the polymerase chain reaction, and cleavage with RE1 to provide a population of relatively small DNA sequences referred to as "amplicons." This stage may be repeated in separate analyses with different restriction endonucleases or different schemes, e.g. fractionation.

The first amplicon of source DNA is referred to as the "driver," which amplicon is used in substantial excess in the subsequent processing of the other, "tester" amplicon. The tester includes the "target" DNA, which DNA does not anneal to driver amplicon. Partially double-stranded PCR adaptors are ligated only to tester amplicon fragments, and the tester and driver DNA combined, melted and reannealed. The termini of the amplicons are filled in and using primers complementary to the adaptors, the DNA mixture is subjected to amplification, wherein the target DNA will undergo exponential amplification and be substantially enriched as compared to driver DNA and non-target tester DNA, which anneals to the driver DNA. Adaptors may then be removed and the cycle repeated using different adaptors. Various modifications may be employed at different stages to further enhance selection of the target DNA.

DESCRIPTION OF THE SPECIFIC EMBODIMENTS

Methods are provided for representational difference analysis ("RDA") between two sources of DNA. The method permits the detection of sequences which differ between the two sources, where under selective conditions of hybridization, DNA from one of the two sources is not significantly hybridized to DNA from the other source. Sources include genomes, sets of DNA fragments, usually $\geq 10$ kbp, collections of restriction endonuclease-cleaved fragments, etc. The method involves a first step, referred to as representation, and then two further steps referred to as subtractive and kinetic enrichment, which may be repeated in order to provide for substantial enrichment of the sequences of interest.

For the purpose of this invention, a number of coined terms will be used. "Driver" DNA is DNA from a source which will be used to determine the presence of DNA in a second source, the "tester" source. Those fragments that are unique to the tester DNA, as compared to the driver DNA, will be referred to as "target" DNA. The DNA sequences are obtained in a first stage resulting from restriction endonuclease digestion, followed by linkage of adaptors and then amplification with primers complementary to the adaptors. The resulting DNAs are referred to as "amplicons." The amplicons will be characterized by being under about 2 kb and usually at least about 0.5 kb, where the termini will normally have the same restriction endonuclease recognition sequence prior to linkage to the adaptors.

The subject application may find use in a wide variety of situations. In determining the presence or absence of particular DNA sequences, particularly associated with recessive or dominant traits, one can compare two related sources of DNA to determine whether they share the particular sequence, where the sequence may be a coding or non-coding sequence, but will be inherited in association with the DNA sequence(s) associated with the trait. One can use the subject method in forensic medicine, to establish similarities between the DNA from two sources, where one is interested in the degree of relationship between the two sources. The subject method can also be applied in the study of diseases, where one can investigate the presence of a sequence associated with infection, such as a viral sequence which may or may not be integrated into the genome. One may also use the subject methodology in studying changes in the genome as a result of cancer, where cancerous cells may be compared to normal wild-type cells. Thus, the subject methodology has application for detecting genetic rearrangements, for identification of DNA from pathogenic organisms integrated into the genome or present in the cellular host, for identification of polymorphisms located at or near genes associated with inherited disorders, and the like.

In carrying out the subject method, there are concerns which should be considered when applying the subject method. The PCR may be a source of artifact, due to the stochastic nature of the process. Therefore, each candidate difference product should be tested for its presence or absence in tester and driver amplicons. Another source of artifact may occur during tissue sampling. Normal flora contaminating a specimen of tester will be readily enriched during difference analysis if that flora is not also present in driver. Genetic mosaicism may be encountered. In situations where one is dealing with polyclonal tissue, such as in cancer, there must be a minimum proportion of cells which has the particular mutation in order to be able to detect the presence of the mutation. Therefore, it would be desirable to use cultures of cancer cells or highly purified cancer cells obtained by physical separation as the source for the tester DNA. In the case of discovery of pathogens, there should be a careful matching of the polymorphisms from the infected and uninfected DNA source.

Tester and/or driver DNA may derive from the same individual, come from an identical twin, come from separate but related individuals, or be the pooled DNA from the parents of the tested individual.

Finally, not all restriction endonucleases will be equivalent in the ease with which target DNA may be identified. Therefore, in each case it will be desirable to use a plurality of restriction endonucleases in separate determinations, not only to ensure that one obtains target DNA within a reasonable number of cycles, but also to increase the number of target DNA sequences that may be obtained.

Turning now to the specific process, the first stage is the isolation of DNA. As already indicated, the DNA may be from any source, eukaryotic or prokaryotic, invertebrate or vertebrate, mammalian or non-mammalian, plant or other higher eukaryotic source. While, for the most part, the sources will be human DNA, the subject methodology is applicable to any complex genome, where one is interested in identifying the presence or absence of related DNA. Normally, the DNAs will be from closely-related sources, so that the number of target DNA sequences which are obtained will be relatively restricted in number, frequently being fewer than about $10^4$, usually fewer than about $10^3$, different sequences In the first stage, the DNA is isolated, freed of protein, and then substantially completely digested with a restriction endonuclease which provides for relatively infrequent cutting. Usually, the restriction endonuclease will have a consensus sequence of at least six nucleotides and may provide for blunt ends or staggered ends, usually staggered ends. Various restriction endonucleases may be employed, such as BamHI, BglII, HindIII, etc. After digestion of the DNA, double-stranded oligonucleotide adaptors are ligated to the ends of each of the strands of the DNA from the driver and the DNA from the tester. The adaptor will usually be staggered at both ends, with one strand being longer and serving as the sequence complementary to the primer. The adaptor will be double-stranded and have one end complementary to the ends of the dsDNA from the digestion. The DNA from the two sources is then separately amplified, by adding primer and using the polymerase chain reaction with extension for the last round, usually employing at least 10 cycles, more usually at least 15 cycles and generally not more than about 30 cycles, more usually not more than about 25 cycles and preferably about 20 cycles. After this number of cycles, for the most part, the fragments will be below about 2 kb, usually below about 1.0 kb. The adaptors are then removed by restriction endonuclease digestion and physical separation, using any convenient means.

As distinct from a physical fractionation, the amount of starting material is not limiting when using representation. When employing amplicons of mammalian DNA after cleavage with BamHI, BglII and HindIII, the estimated complexity of the resulting amplicons are 55-fold, 13-fold and 8-fold less than the complexity at the starting genomic DNA, respectively (Bishop, et al., *Am. J. Hum. Genet.* 35, 795 [1983]).

In the next phase, subtractive and kinetic steps are employed in a single operation of hybridization and amplification. If desired, the steps may be separated, but will preferably be done contemporaneously. The first aspect of this stage is the ligation of PCR adaptors to the ends of tester amplicon fragments or the products of previous rounds of enrichment, when the procedure is reiterated. Usually, the adaptor chain complementary to the primer will be at least about 12 nt, more usually at least 17 nt, and generally fewer than about 200 nt, more usually fewer than about 100 nt. Any convenient method for ligation of the adaptors to the 5' ends may be employed, as appropriate.

The tester amplicon fragments joined to the adaptors are then combined with the driver amplicon fragments and melted and allowed to reanneal. The driver amplicon fragments will be present in substantial excess, usually at least 5-fold excess, and the excess may exceed 50 or more, usually not exceeding about $10^8$-fold excess, more usually not exceeding 500-fold excess. The ratio of driver DNA to tester DNA need not be constant for the different rounds. Usually, the ratio will increase with successive rounds where the increase may vary from about 1:1 to $10^3$. Usually the initial ratio will be in the range of about 10 to 1000-fold excess. Usually, melting will be achieved by heating at an elevated temperature, generally $\geq 95°$ C. and hybridization proceeding at about 60° C., where various buffers may be employed, as well as salt concentrations, to provide the necessary stringency. Usually, fairly high stringencies will be employed, generally at least about equivalent to or greater than about 0.1M NaCl, usually about 1M NaCl.

After melting and reannealing, there will be a substantial enrichment of target DNA in the total double-stranded DNA, since the target DNA will not be inhibited from self-annealing due to the lack of complementary sequences present in the driver DNA.

Overhangs are then filled in by employing any convenient DNA polymerase, e.g. Taq DNA polymerase, in the presence of the four nucleotides, whereby only double-stranded, self-reannealed tester DNA will have filled-in adaptors at each end of the amplicon. Since the driver DNA does not inhibit target DNA from self-annealing, while the driver DNA inhibits non-target tester DNA from self-annealing, there is a substantial enrichment in the target DNA as compared to the total tester DNA.

The double-stranded self-reannealed tester amplicon will then be amplified under conventional polymerase chain reaction conditions, usually involving at least about 5 cycles, frequently as many as 10 cycles and usually not more than about 40 cycles, preferably not more than about 30 cycles. The amplification may be interrupted about midway and single-stranded DNA degraded using an appropriate nuclease. Various nucleases may be employed, particularly mung bean nuclease.

The resulting double-stranded DNA mixture may then be digested with a restriction endonuclease which removes the adaptors from the tester DNA. The tester DNA may be separated from the adaptor sequence, using any convenient means which permits separation by size. Gel filtration or gel electrophoresis may be conveniently employed. The amplicons may then be ligated to a second set of adaptors, usually different from the first or previous set and the cycle of melting in the presence of excess driver amplicon, annealing, filling in overhangs, and PCR amplification repeated. Later cycles may rely on the previous adaptors. In the subject process, this cycle may be repeated one or more times, there usually being at least 2 rounds or repetitions and not more than about 6 rounds, usually 2 to 4 rounds being sufficient.

It will frequently be of interest to carry out the process more than once, where different restriction endonucleases are employed for each study. In this way, different amplicons will be obtained and one may obtain different information. Depending upon the purpose for the process, two or more restriction endonucleases may be utilized in separate preparations of the amplicons. One may also compare the probes obtained with different restriction endonucleases to determine if they overlap, bind to genomic DNA sequences which are proximal, are part of the same gene or polymorphic region, and the like.

In carrying out the process, the first round is mainly subtractive. Subsequent rounds have a greatly-increased component of kinetic enrichment. For example, if target DNA is equimolar with respect to tester DNA (i.e. a single copy), and if driver amplicon is taken in N-fold excess to tester amplicon, assuming virtually complete reannealing of driver amplicon, target will be enriched N times after the first round. After the second round, target will be enriched $N^2$ multiplied by a factor due to the subtractive component, and after the third time, at least the square of that. If N is 50, at the end of the second round, target will be enriched by about $10^4$, and at the end of the third round, on the order of $10^8$. In general a single cycle of subtraction can be expected to yield enrichments of target in the order of fN, where N is the molar excess of driver amplicon to tester amplicon and f is the fraction of driver amplicon that reanneals.

The resulting target DNA may be used as probes to identify sites on the tester DNA genome which differ from the driver DNA. For this purpose, they may be labeled in a variety of ways, such as with radioactive labels, biotin, fluorescers, etc. Desirably, in order to obtain substantially homogeneous compositions of each of the target amplicons, the target amplicons may be cloned by inserting into an appropriate cloning vector for cloning in a prokaryotic host. If desired, the cloned DNA may be sequenced to determine the nature of the target DNA. Alternatively, the cloned DNA may be labeled as described above, and used as probes to identify fragments in libraries carrying the target DNA. The target DNA may be used to identify the differences which may be present between the two sources of DNA.

In pedigree analysis, the, subject process may be used to define sequences which are present in one member of a family and not present in another. In this way, one may then compare other members of the family as to whether they carry the same DNA or it is absent. This may find use in forensic medicine, where there may be an interest in the relationship between two individuals, a sample obtained from a source and an individual, or the like.

The subject method can also be used to construct libraries of probes for genetic polymorphisms, which may be referred to as PARFs, which is operationally defined as a polymorphic restriction endonuclease fragment, present in the amplified DNA from one genome and not present in the amplified DNA from a different genome from a like organism. For example, if one of two BamHI sites flanking a short BamHI fragment in tester DNA is absent in both alleles from driver DNA, leading to only large BamHI fragments in driver, the short BamHI fragment of tester will be present in its BamHI amplicon, but absent in the BamHI amplicon of the driver. Thus, the restriction fragment would directly lead to a probe which will distinguish between the two genomes.

It should be appreciated, that where the amplicons are cloned, there may be substantial redundancy in individually-picked clones. Therefore, the efficiency of selecting different probes will vary substantially depending upon the frequency in which the amplicon was present in the mixture prior to cloning, which may be as a result of the varied efficiency of amplification, or other artifacts which are built into the methodology.

The subject method can be used to isolate probes for pathogens, where DNA which is suspected of being infected may be compared to DNA which is believed to be uninfected. For example, if one were interested in a virus which is tropic for a particular cell type or tissue, e.g. HIV for T-cells and macrophages or hepatitis B virus for liver, one could take tissue from the source suspected of infection for which the virus is tropic and tissue from another site in the same individual, where such virus should not be present. By carrying out the process, one should obtain probes which would be specific for the virus, since by appropriate selection of the sources of the cells, one would not anticipate any other differences.

A limitation of the subject process, which will be applicable to viruses, as well as other situations, is that the population carrying the target DNA should be a reasonable proportion of the total number of cells from which the tester DNA is derived. As indicated above, where one is interested in the presence of integrated pathogenic DNA, it may be that only a small proportion of these cells in the tissue are infected. It may, therefore, be desirable to normalize the tester sequences, in order to equalize the concentrations of all tester sequences, prior to the subtractive and kinetic enrichment (Patanjali, et al., *Proc. Natl. Acad. Sci. USA* 88, 1943 [1991]).

Application of RDA to the discovery of pathogens requires a careful matching of the polymorphisms from the infected and uninfected DNA sources. Tester and driver DNA can derive from the same individual, if the individual is not a genetic mosaic. These DNAs cannot derive from unrelated individuals, as the abundant polymorphic differences in their DNAs would obscure the detection of the pathogen. However, the uninfected DNA source (driver) could, in principle, come from an identical twin, or be the pooled DNA from the parents of the infected individual, because virtually all of the DNA restriction fragments found in the genomic DNA of the infected individual can be expected to be present in at least one parent DNA.

The subject methodology may be also be applied to detecting genomic alterations occurring in cancer cells. These could be of two distinct types: those that result in loss of restriction endonuclease fragments, such as might occur from deletions or gene conversions extending over heterozygous polymorphisms, and those that produce new restriction endonuclease fragments, such as might result from genomic rearrangements. In the former case, RDA could be applied without modifications using DNA from cancer cells as driver and normal DNA as tester. Unfortunately, the presence of normal stroma in a cancer biopsy could interfere with the detection of loss of genetic information in the cancer cell. Hence, either cultures of cancer cells or highly-purified cancer cells obtained by physical separation would be needed as the source for tester.

These restraints do not apply to the detection of genomic rearrangements. Genomic rearrangements, including translocations, insertions, inversions and deletions, will result in the creation of new restriction endonuclease fragments bridging the site of the rearrangement. Some of these bridging fragments may be amplifiable, while at least one of the fragments from which they derive in normal DNA is not. Such bridging fragments would be discoverable by RDA, when DNA from the tumor is used for preparation of tester amplicons and DNA from normal tissue of the same individual is used for preparation of driver amplicons.

The different-sized restriction endonuclease fragments created by genomic rearrangements may be exploited another way. Fractionated size classes from tumor DNA digests will sometimes contain sequences that are not present in comparable-size classes from normal DNA. Using the former as tester and the latter as driver, one can prepare amplicons after cleavage with a second restriction endonuclease and compare these by RDA in order to clone amplifiable restriction endonuclease fragments in proximity to the point of genetic rearrangement. With either of the above-indicated methods, the presence of normal cells among the tumor cells will not obscure the detection of probes for the rearrangement.

When RDA is applied to different individuals, it will yield a collection of polymorphisms of a type, which has been previously referred to as PARFs. Thus, RDA can be used for generating new sets of polymorphisms, not only for species that have not previously undergone extensive molecular genetic characterization, but also for well-studied species as humans and mice. Since PARFs most often detect binary polymorphisms, they can serve as a panel of probes that can be used with a standardized format for genetic typing.

In yet another application, RDA can yield probes for PARFs present in the DNA of an individual from a founder group affected by some autosomal dominant inherited disorder (the tester), but absent in the DNA of an individual from a normal group (the driver). Conversely, RDA can yield probes for PARFs present in the DNA of a normal individual (the tester), but absent in the DNA of an individual from the founder group affected by a recessive inherited disorder (the driver). Combined with methodologies for coincidence cloning (Brooks and Porteous, *Nuc. Acid Res.* 19, 2609 [1991]), such applications can accelerate the discovery of probes for rare PARFs in linkage disequilibrium with the dominant locus, or the absence of common PARFs in linkage disequilibrium with the recessive locus.

Other applications may involve spontaneous germ line genomic rearrangements. The genome of such an infected individual will include restriction endonuclease fragments that are present in neither parent. This situation is analogous to genetic rearrangements occurring in cancer cells, which has been previously discussed.

To ensure that the subject process has operated properly, it will normally be desirable to test candidate difference products (target DNA) for its presence or absence in tester and driver amplicons. Also of concern will be the presence of flora, which may contaminate tester, but is not present in driver. Genetic mosaicism will also interfere with the subject methodology. However, in a wide variety of contexts, the subject method will efficiently provide sequences which can be used for analyzing differences between two genomes as a result of a wide variety of events.

The following examples are offered by way of illustration and not by way of limitation.

EXPERIMENTAL

Preparation of Amplicons. 10 μg of high molecular weight DNA purified from the lymphoid cell line DRL 4824 (a gift of T. Caskey, Baylor College) was used for preparation of driver amplicons and 10 μg of the same DNA, containing equimolar amounts of target (120 pg of adenovirus-2 DNA and/or 160 pg of λ phage DNA, both from New England Biolabs) was taken for preparation of tester amplicons. Both tester and driver DNA samples were digested with restriction endonuclease (New England Biolabs) and 1 μg of each DNA digest was mixed with 0.5 nmoles of 24-mer and of 12-mer unphosphorylated oligonucleotides (set 1 (SEQ. ID NOS:1–2,7–8,13), see Table 1) in 30 μL of T4 DNA ligase buffer (New England Biolabs).

TABLE 1

Sequences of Primers Used for Representational Difference Analysis.

| Primer Set | Name | Sequence |
|---|---|---|
| 1 | R Bgl 24 | 5'-AGCACTCTCCAGCCTCTCACCGCA-3' (SEQ ID NO: 1) |
| | R Bgl12 | 5'-GATCTGCGGTGA-3' (SEQ ID NO: 2) |
| 2 | J Bgl24 | 5'-ACCGACGTCGACTATCCATGAACA-3' (SEQ ID NO: 3) |
| | J Bgl12 | 5'-GATCTGTTCATG-3' (SEQ ID NO: 4) |

TABLE 1-continued

Sequences of Primers Used for Representational Difference Analysis.

| Primer Set | Name | Sequence |
|---|---|---|
| 3 | N Bgl24 | 5'-AGGCAACTGTGCTATCCGAGGGAA-3' (SEQ ID NO: 5) |
|   | N Bgl12 | 5'-GATCTTCCCTCG-3' (SEQ ID NO: 6) |
| 1 | R Bam24 | 5'-AGCACTCTCCAGCCTCTCACCGAG-3' (SEQ ID NO: 7) |
|   | R Bam12 | 5'-GATCCTCGGTGA-3' ∝ (SEQ ID NO: 8) |
| 2 | J Bam24 | 5'-ACCTGACGTCGACTATCCATGAACG-3' (SEQ ID NO: 9) |
|   | J Bam12 | 5'-GATCCGTTCATG-3' (SEQ ID NO: 10) |
| 3 | N Bam24 | 5'-AGGCAACTGTGCTATCCGAGGGAG-3' (SEQ ID NO: 11) |
|   | N Bam12 | 5'-GATCCTCCCTCG-3' (SEQ ID NO: 12) |
| 1 | R Hind24 | Same as R Bgl24 (see above) (SEQ ID NO. 1) |
|   | R Hind12 | 5'-AGCTTGCGGTGA-3' (SEQ ID NO: 13) |
| 2 | J Hind24 | Same as J Bgl24 (see above) (SEQ ID NO. 3) |
|   | J Hind12 | 5'-AGCTTGTTCATG-3' (SEQ ID NO: 14) |
| 3 | N Hind24 | 5'-AGGCAGCTGTGGTATCGAGGGAGA-3' (SEQ ID NO: 15) |
|   | N Hind12 | 5'-AGCTTCTCCCTC-3' (SEQ ID NO: 16) |

Primer set 1 (R series) is used for representations, and sets 2 (J series) and 3 (N series) are used for odd and even hybridization/amplifications, respectively. Oligonucleotide design was checked for the absence of strong secondary structure using the OLIGO computer program (National Biosciences).

Oligonucleotides were annealed by cooling the mixture gradually from 50° C. to 10° C. for one hour and then ligated to human DNA fragments by overnight incubation with 400 U of T4 DNA ligase at 16° C. Following ligation, both tester and driver DNA samples were amplified. Each of 10 tubes taken for preparation of driver amplicons and 2 tubes used for preparation of tester amplicons contained in a volume of 400 μl: 67 mM Tris-HCl, pH 8.8 at 25° C., 4 mM MgCl$_2$, 16 mM (NH$_4$)$_2$SO$_4$, 10 mM β-mercaptoethanol, 100 μg/ml bovine serum albumin, 200 μM (each) dATP, dGTP, dCTP, and dTTP, 1 μM 24-mer primer and 80 ng of DNA with ligated adaptors. The tubes were incubated for 3 min. at 72° C. in a thermal cycler (Perkin Elmer Cetus), 15 U of Taq polymerase (AmpliTaq, Perkin Elmer Cetus) was added, the reactions were overlaid with mineral oil, incubated for 5 min. to fill in 5' protruding ends of ligated adaptors, and amplified for 20 cycles (each cycle including 1 min. incubation at 95° C. and 3 min. at 72° C., with the last cycle followed by an extension at 72° C. for 10 min.). After amplification both driver and tester amplicons were digested with the same restriction endonuclease (10 U/μg) to cleave away adaptors. 10 μg of tester amplicon DNA digest was electrophoresed through 2% NuSieve agarose (low melting point, FMC Bio Products), and DNA fragments (150–1500 bp) were recovered after melting of the agarose slice and Quiagen-tip20 chromatography (Quiagen Inc.) to remove adaptors. These fragments were ligated to a new set of adaptors (primer set 2 (SEQ ID NOS:3–4,9–10, 14), see Table 1) in preparation for the first round of hybridization and amplification.

DNA Hybridization and Amplification Step. 0.5 μg of the tester amplicon DNA ligated to adaptors and 40 μg of driver amplicon DNA were mixed, ethanol precipitated, dissolved in 4 μl of 3×EE buffer (Straus and Ausbel, Proc. Natl. Acad. Sci. USA 87, 1889 [1990]) and overlaid with 30 μl of mineral oil (Perkin Elmer Cetus). Following heat denaturation 1 μl of 5M NaCl solution was added and DNA was hybridized for 20 h at 67° C. At the end of hybridization, 1/10th part of the resulting DNA was incubated with 15 U of Taq polymerase (5 min., 72° C.) in 400 μl of PCR mixture without primer to fill in ends of reannealed tester, and then amplified for 10 cycles (1 min. at 95° C., 3 min. at 70° C., followed by 10 min. extension for the last round) after addition of the same 24-mer oligonucleotide to which tester was ligated. Single stranded DNA molecules present after amplification were degraded by 30 min. incubation with 20 U of mung bean nuclease (New England Biolabs) in a volume of 40 μl as recommended by the supplier followed by 5-fold dilution of the sample in 50 mM Tris-HCl pH 8.9 and heat inactivation of enzyme (95° C., 5 min.). 40 μl of the solution was amplified for 15–20 cycles under the same conditions as before the mung bean nuclease treatment. Amplified DNA (3–5 μg) was digested with the original restriction endonuclease and 200 ng of the digest was ligated to the third adaptor set (SEQ ID NOS:5–6, 11-12, 15-16) (see Table 1). 50–100 ng of this DNA was mixed with 40 μg of driver amplicon and the hybridization and amplification procedures were repeated as in the first cycle. 200 ng of the digest obtained after the second hybridization/amplification step was then ligated to the second set of adaptors (SEQ ID NOS:3–4, 9–10, 14) and 100–400 pg of this material together with 40 μg of driver amplicon was taken for the third round of hybridization, with the final amplification after mung bean nuclease digestion for 20–25 cycles. A fourth hybridization/amplification step was performed after taking 5 pg of material from the third round ligated to adaptors of the third set (SEQ. ID NOS:5–6, 11–12, 15–16) and mixing it with 40 μg of driver amplicon.

EXAMPLE 1

Representational Difference Analysis with Viral DNAs Added as Targets.

Single-copy levels of adenovirus and/or bacteriophage λ DNA was added to human DNA to create a model tester, and used with the same human DNA without viral DNA as driver. BglII amplicons from human DNA with adenovirus and λ DNAs as targets or HindIII amplicons with λ DNA as target were prepared. With BglII amplicons, small λ and adenovirus fragments were the major difference products, even after two rounds, as evidenced by agarose gel electrophoresis. This represented an enrichment of $>5\times10^6$-fold from the starting material and a probable enrichment of about $4\times10^5$-fold from amplicons.

The enrichment from HindIII amplicons was not as effective. The λ HindIII fragment was greatly enriched after the third round as evidenced by blot hybridization, but still not to homogeneity. After the fourth round the expected target fragment was purified to near homogeneity. The difference between the experience with the HindIII restriction endonuclease and the BglII restriction endonuclease may be related to the greater sequence complexity of the HindIII amplicons. When the complexity of the driver is too high, subtractive and kinetic enrichments are diminished and competing processes may dominate. The competing processes may involve the emergence of efficiently-amplified repetitive sequences in tester.

EXAMPLE 2

Representational Difference Analysis of DNAs from Two Individuals.

Driver and tester amplicons were prepared from human lymphoblastoid cell cultures GM05901 and GM05987, respectively (Amish Pedigree 884, Human Genetic Mutant Cell Repository, Camden, N.J.). Amplicons were prepared after cleavage with BamHI, BgiII or HindIII. Difference products between amplicons were obtained as described above and size fractionated by gel electrophoresis. A discrete but complex pattern of bands was observed in each case. After three hybridizations/amplifications, difference products were cloned into plasmids. For each difference product, three probes were picked for blot hybridization analysis. It was found that all of them were polymorphic within the Amish family data. BamHi difference products were analyzed in greatest detail.

DNAs extracted from cell lines or placentas (Table 2). Complete concordance between this method and Southern blotting of total genomic DNA was found. These results support the conclusion that the probes which detect polymorphisms within the Amish family will also detect polymorphisms in the human population at large. As indicated previously, these polymorphisms are referred to as PARFs (polymorphic amplifiable restriction endonuclease fragments).

The probes for PARFs are not equally abundant in the difference product. To obtain a measure of this unevenness, each cloned BamHI PARF was hybridized to a grid of 90 individually randomly-picked clones from the difference product of the two siblings, and its frequency in the collection was determined (see percent value in Table 2). From a total of 90 randomly-picked elements, only 20 distinct polymorphic probes were present.

It should be noted that the protocol was designed for the detection of a small number of differences between two nearly-identical genomes. Where probes for polymorphic loci are deliberately sought, more representative difference products can be generated by diminishing the number of rounds of hybridization/amplification, increasing the complexity of the representation and/or decreasing the total number of PCR cycles.

TABLE 2

Screening for Presence of BamHI PARFs in 17 Human DNA Samples.

| Probe Number (%) | A | B | C | D | E | F | G | H | I | J | K | L | M | N | O | P | Q | Length of alleles in kbp Large | Small |
|---|---|---|---|---|---|---|---|---|---|---|---|---|---|---|---|---|---|---|---|
| 1 (15.5) | − | + | − | + | + | + | + | + | + | + | + | + | + | + | + | + | + | 15 | 0.61, 0.67(a) |
| 11 (14.4) | − | + | − | − | + | + | − | − | − | − | − | − | − | − | − | − | − | 15 | 0.6 |
| 6 (8.9) | − | + | + | − | + | + | + | + | + | + | + | − | + | − | + | − | + | 3.5 | 0.58 |
| 19 (5.5) | − | + | + | − | + | + | + | + | + | + | − | + | − | − | + | + | + | 15 | 0.51 |
| 17 (4.4) | − | + | − | − | + | + | + | + | + | − | − | − | − | − | − | − | + | 8 | 0.48 |
| 22 (4.4) | − | + | + | + | − | + | + | + | − | + | + | + | + | − | + | + | + | 6.5 | 0.67 |
| 8 (3.3) | − | + | + | + | − | + | + | + | + | + | − | − | − | − | + | + | + | ND | 0.62 |
| 24 (3.3) | − | + | − | − | − | − | − | − | − | + | + | − | + | + | − | + | − | >50 | 0.65 |
| 26 (3.3) | − | + | + | − | − | − | + | + | + | + | − | + | − | + | + | + | − | 6, 5(b) | 0.65 |
| 9 (2.2) | − | − | − | − | − | + | − | + | − | − | − | − | − | − | − | − | − | ND | 0.47 |
| 65 (2.2) | − | + | + | + | − | + | + | + | + | + | + | + | + | − | + | + | + | 4 | 0.74 |
| 3 (1.1) | − | + | + | + | − | + | + | + | + | + | − | + | − | + | + | + | − | ND | 0.5 |

BamHI amplicons were prepared from DNA from seven Amish pedigree lymphoblastoid cell cultures, GM05901 (driver), GM05987 (tester), GM05918, GM05961, GM05963, GM05993, GM05995 (columns A−G), five different placentas (columns H−L), three lymphoblastoid cell lines established from the biopsies of leukemic patients (columns M, N, O) and two fibroblast cell cultures, DRL 484, and DRL 569 (a gift of T. Caskey, Baylor College) established from the biopsies of DMD patients (columns P, Q), transferred to GeneScreen membrane, and hybridized to the indicated probes. "%" indicates the percent of clones in a DWHI PARF collection of difference products cloned after three hybridization-amplification steps that hybridized to the indicated clone. "+" means that the small BamHI PARF allele was present in the sample (i.e. the probe hybridized to a band of the correct size in the amplicon); "−" means that the small allele was not detected. See FIG. 3C for a sample of the actual data. The lengths of the alleles hybridizing to PARFs are indicated, where known. "ND" means not determined.
(a) Two different small alleles were found in the human population.
(b) Two different large alleles were found in the human population.

Of 20 randomly-picked clones, 12 unique clones remained after removing redundancies, and the inserts from 9 of these were used as probes in Southern blots of tester, driver and 5 other members of the family (GM05918, GM05987 [tester], GM05901 [driver], GM05961, GM05963, GM05993, and GM05995 from Amish pedigree 884). All probes detected small BamHI fragments in the tester (Table 2, col. B) and only large BamHI fragments in the driver (Table 2, col. A). The blot hybridization pattern for each probe was completely consistent with a Mendelian pattern of inheritance. The results demonstrate that collections of probes for restriction endonuclease fragment polymorphisms may be obtained between two related individuals.

Each of the BamHI probes derived from the above experiment was also used in blot hybridizations to amplicons from the family and 10 other unrelated human It is evident from the above results, that a powerful tool has been provided for isolating probes which can be used to identify sequence differences between two related genomes. This technique may be used in a wide variety of contexts in relation to forensic medicine, detecting the presence of integrated pathogenic DNA, lesions resulting from neoplastic cells, genetic counseling, the presence of genes associated with genetic diseases, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for producing probes capable of distinguishing at least one sequence difference between DNA from two different eukaryotic sources, said method comprising:
   completely digesting separately the DNA from said two different sources with a restriction endonuclease to provide digested fragments, wherein one of said sources is driver DNA, and the other source is tester DNA, wherein said tester DNA comprises target DNA, wherein said target DNA comprises sequence differences between the genomes of said two sources;
   ligating a first set of adaptors to said digested fragments and amplifying said fragments by means of the polymerase chain reaction using primers to one of the strands of said first set of adaptors to provide amplified amounts of fragments of said digested fragments of less than about 2 kbp as amplicons;
   carrying out a first round of the following steps for enrichment of target DNA:
   removing said first set of adaptors from said amplicons and ligating a second set of adaptors to amplicons of tester DNA;
   combining under melting and annealing conditions said tester amplicons with a large excess of at least about 5 fold of driver amplicons, whereby a portion of the resulting dsDNA comprises self-annealed tester DNA including target DNA;
   amplifying by means of the polymerase chain reaction said portion of said dsDNA with primers complementary to one of said strands of said second set of adaptors to enrich for target DNA;
   optionally repeating said first round of steps as a second round or successive round, to provide DNA sequences which serve to identify differences in DNA sequences between said tester source and said driver source.

2. A method according to claim 1, including the additional step during said amplifying of said portion of said dsDNA of adding a nuclease for digesting single stranded DNA present with said portion of said dsDNA.

3. A method according to claim 1, wherein said first round of steps is repeated at least once.

4. A method according to claim 3, wherein said first round is repeated at least twice for a total of at least three rounds and different sets of adaptors are used for at least said first three rounds.

5. A method according to claim 1, wherein said digesting is with a restriction endonuclease which has a recognition sequence of at least 6 nucleotides and provides a staggered cleavage.

6. A method according to claim 1, wherein the sources of DNA are cells from related human individuals or the same individual.

7. A method for producing probes capable of distinguishing at least one sequence difference between genomes from two human cellular sources, said method comprising:
   completely digesting separately the DNA from said two human cellular sources with a restriction endonuclease to provide digested fragments, wherein one of said sources is driver DNA, and the other source is tester DNA, wherein said tester DNA comprises target DNA, wherein said target DNA comprises sequence differences between the genomes of said two sources;
   ligating a first set of adaptors to said digested fragments and amplifying by means of the polymerase chain reaction said fragments using primers to one of the strands of said first set of adaptors to provide amplified amounts of fragments of said digested fragments of less than about 2 kbp as amplicons;
   carrying out a first round of the following steps for enrichment of target DNA;
   removing said first set of adaptors from said amplicons and ligating a second set of adaptors to amplicons of tester DNA;
   combining under melting and annealing conditions said tester amplicons with a large excess of at least about 5 fold of driver amplicons, whereby a portion of the resulting dsDNA comprises self-annealed tester DNA including target DNA;
   amplifying by means of the polymerase chain reaction said portion of said dsDNA with primers complementary to one of said strands of said second set of adaptors to enrich for target DNA;
   repeating said first round of steps for at least one additional time for a total of at least 2 rounds, using a different set of adaptors in each successive round for said 2 rounds to provide a DNA composition comprising a further enriched amount of target DNA; and
   cloning said DNA composition to provide clones having a homogeneous probe of target DNA.

8. A method according to claim 7, wherein said human cellular sources are from the same individual and differ as to the suspected presence of a pathogen.

9. A method according to claim 7, wherein said related human cellular sources are from the same individual and differ as to the suspected presence of a genetic lesion.

10. A method according to claim 7, wherein said related human cellular sources are from two different individuals.

11. A method according to claim 7, wherein one of said cellular sources is cancer cells.

12. A method according to claim 11, wherein said cancer cells are from cultures of said cancer cells or purified cancer cells.

13. A method according to claim 7, wherein one of said cellular sources is suspected of comprising a virus integrated into the genome of said cellular source.

14. A method according to claim 7, including the additional step of probing DNA from a third human cellular source with said probe, wherein said third human cellular source is different from said two human cellular sources.

* * * * *